United States Patent
Yamaguchi et al.

(10) Patent No.: US 8,003,369 B2
(45) Date of Patent: Aug. 23, 2011

(54) BACTERIOLYTIC AGENT

(75) Inventors: Shunichiro Yamaguchi, Kyoto (JP); Shuji Miura, Kyoto (JP); Hiroaki Maeda, Kyoto (JP)

(73) Assignee: Sanyo Chemical Industries, Ltd., Kyoto-shi (JP)

( * ) Notice: Subject to any disclaimer, the term of this patent is extended or adjusted under 35 U.S.C. 154(b) by 122 days.

(21) Appl. No.: 12/092,610

(22) PCT Filed: Nov. 6, 2006

(86) PCT No.: PCT/JP2006/322512
§ 371 (c)(1), (2), (4) Date: May 5, 2008

(87) PCT Pub. No.: WO2007/063691
PCT Pub. Date: Jun. 7, 2007

(65) Prior Publication Data
US 2009/0143569 A1    Jun. 4, 2009

(30) Foreign Application Priority Data
Nov. 29, 2005 (JP) ................. 2005-344659

(51) Int. Cl.
*C12N 1/06* (2006.01)

(52) U.S. Cl. ............................................. 435/259

(58) Field of Classification Search ............... None
See application file for complete search history.

(56) References Cited

U.S. PATENT DOCUMENTS

| | | | |
|---|---|---|---|
| 4,678,605 A | 7/1987 | Geke et al. | |
| 6,087,303 A * | 7/2000 | Walker | 504/158 |
| 2002/0142425 A1 | 10/2002 | Miyake et al. | |
| 2004/0067574 A1 | 4/2004 | Bijl et al. | |
| 2004/0101947 A1 | 5/2004 | Engel et al. | |

FOREIGN PATENT DOCUMENTS

| | | |
|---|---|---|
| EP | 0 576 294 A2 | 12/1993 |
| GB | 2 168 374 A | 6/1986 |
| JP | 05-064584 A | 3/1993 |
| JP | 06-153947 A | 6/1994 |
| JP | 07-233393 A | 9/1995 |
| JP | 2002-119288 A | 4/2002 |
| JP | 2002-199885 A | 7/2002 |
| JP | 2002-335969 A | 11/2002 |
| WO | 02/06456 A1 | 1/2002 |
| WO | 2004/042003 A2 | 5/2004 |

OTHER PUBLICATIONS

International Search Report of PCT/JP2006/322512; date of mailing Dec. 5, 2006.
Notification of Transmittal of Translation of the International Preliminary Report on Patentability (Form PCT/IB/338) of International Application No. PCT/JP2006/322512 mailed Jun. 12, 2008 with Forms PCT/IB/373 and PCT/ISA/237.
Japanese Office Action on JP 2005-344659 dated Mar. 31, 2009.
Japanese Office Action on JP 2005-344659 dated Jun. 24, 2009.

* cited by examiner

*Primary Examiner* — Nita M Minnifield
*Assistant Examiner* — Brian J Gangle
(74) *Attorney, Agent, or Firm* — Westerman, Hattori, Daniels & Adrian, LLP

(57) ABSTRACT

The present invention is a bacteriolytic agent containing a cationic surfactant (A) of which a counteranion is an acid having a pKa (25° C.) of 0 to 10. As the counterion, a carboxylate anion is preferable. As the cationic surfactant (A), a quaternary ammonium salt-type surfactant is preferable. Examples of the useful substance include a protein, an amino acid, a nucleic acid, an antibiotic, sugars or vitamins.
The bacteriolytic agent of the present invention is excellent in a bacteriolytic power in a step of extracting a useful substance from a microorganism (useful substance producing bacterium etc.). In addition, denaturation of the useful substance during the step is small.

2 Claims, No Drawings

BACTERIOLYTIC AGENT

TECHNICAL FIELD

The present invention relates to a bacteriolytic agent used when a useful substance such as a protein is extracted from a useful substance-producing bacterium, and a process for producing the useful substance.

BACKGROUND ART

A microorganism is widely utilized as a host for production of a useful substance such as an amino acid, a protein and the like. Particularly, in recent years, a technique for effectively manufacturing a useful substance using a transformed microorganism having a gene of an industrial useful protein introduced therein by utilizing the genetic engineering technique has been known.

Examples of a preferable microorganism producing a useful substance include a gram-negative bacteria such as *Escherichia coli*, a *Pseudomonas* bacterium and the like, a gram-positive bacteria such as a *Bacillus* bacterium, a lactic acid bacterium and the like, a yeast such as *Saccharomyces, Candida* and the like, a filamentous fungi such as *Aspergillus, Penicillium* and the like, and an Acitinomyces such as *Streptomyces, Rhodococcus* and the like.

A first stage in purification of a useful substance such as a protein and the like is a stage of lysing a cell producing these useful substances to release cell components.

As a method of lysing a cell, there are a physical method and a chemical method. Among them, as a chemical cell lysing method, there is a method of destructing integrity of a cell membrane or a cell wall using a surfactant.

As a proposed nonionic surfactant, there are nonionic surfactants having a sugar chain (e.g. Japanese Patent Application Laid-Open (JP-A) No. 2004-504330), an alkylamine ethylene oxide adduct (e.g. JP-A NO. 2002-119288), a sorbitan fatty acid ester ethylene oxide adduct (e.g. JP-A No. 6-153947), and the like. As an ionic surfactant, in addition to a cationic surfactant such as a quaternary ammonium salt (e.g. JP-A No. 2002-335969) and the like, an anionic surfactant and an amphoteric surfactant are proposed (e.g. JP-A No. 2002-199885, JP-A No. 5-64584).

However, there was a problem that, in the conventional method using a nonionic surfactant, since bacteriolytic power was insufficient, the method was not suitable for synthesis at a large scale. In addition, in the conventional method using an ionic surfactant, an extracted useful substance such as a protein and the like was denatured, and there was a problem that a three-dimensional conformation was disintegrated.

DISCLOSURE OF THE INVENTION

In order to solve the aforementioned problems, the present inventors intensively studied and, as a result, found out a bacteriolytic agent which is excellent in bacteriolytic power, and can release and extract a useful substance of high quality without denaturation of the useful substance, by using a cationic surfactant of which counteranion has a specified range of a pKa, resulting in the present invention.

That is, the present invention is a bacteriolytic agent including a cationic surfactant of which counteranion is an acid having a pKa of 0 to 10 at 25° C., a process for producing a useful substance from a microorganism using the bacteriolytic agent, and a useful substance produced by the production process.

The bacteriolytic agent of the present invention has bacteriolytic power which is improved more than the conventional one, particularly as a bacteriolytic agent for extracting a useful substance from a useful substance-producing bacterium such as *Escherichia coli* and the like, and more rarely denatures a useful substance than the conventional one.

Therefore, a useful substance of high quality, for example, an enzyme having a small degree of denaturation and high activity can be obtained. In addition, productivity of sugars and the like is better.

BEST MODE FOR CARRYING OUT THE INVENTION

An essential component of the bacteriolytic agent of the present invention is a cationic surfactant (A) whose counteranion is an acid having a pKa of 0 to 10 at 25° C., and cationic part has a hydrophobic group.

Examples of the counterion of the cationic surfactant (A) according to the present invention include a carboxylate anion ($COO^-$), a phosphate anion ($PO_4^{3-}$), a boronate anion ($BO_3^{2-}$), a carbonate anion ($CO_3^{2-}$), a hydroxylate anion ($OH^-$), and the like.

A pKa can be determined by acid-base titration (pH titration or potential difference titration). Specifically, an acidic aqueous solution containing a sample is titrated with an alkali aqueous solution, a pH or a potential difference corresponding to a titration amount is read, and a pKa can be calculated from an inflection point.

The pKa is an acid dissociation constant and, in the case of an acid of multi-stage dissociation, means a first stage dissociation constant. For example, in the case of adipic acid, since the acid is two-stage-dissociated, and the acid dissociation constant can be calculated to be 4.4 (pKa1) and 5.3 (pKa2), the pKa is 4.4.

$$H_nA \rightarrow H_{(n-1)}A^- + H^+$$

$$Ka = [H_{(n-1)}A^-] \times [H^+]/[H_nA]$$

$$pKa = -\log(Ka)$$

Examples of an anion of an acid having a pKa of 0 to 10 include anions of carboxylic acid, phosphoric acid, boric acid, and the like. Specific acids, and their numerical values of a pKa will be listed later.

In the bacteriolytic agent, as a counteranion in a cationic surfactant (A) which is an essential component, a carboxylate anion consisting of a monovalent carboxylic acid or 2- to 8-valent polyvalent carboxylic acid is preferable. This carboxylate anion is an ion having a —$COO^-$ ion obtained by removing a proton from a carboxylic acid.

Examples of a carboxylic acid constituting the carboxylate anion include the following monovalent carboxylic acid and polyvalent carboxylic acid.

<Monovalent Carboxylic Acid>

Examples include aliphatic saturated monocarboxylic acid (formic acid, acetic acid, propionic acid, butyric acid, isobutyric acid, valeric acid, caproic acid, enanthic acid, caprylic acid, pelargonic acid, lauric acid, myristic acid, stearic acid, behenic acid, 2-ethylhexanoic acid, etc.); aliphatic unsaturated monocarboxylic acid (oleic acid, etc.); aliphatic oxy-monocarboxylic acid (glycolic acid, lactic acid, gluconic acid, etc.); amino acid (glycine, alanine, leucine, etc.); and the like.

<Polyvalent Carboxylic Acid>

Examples include aliphatic saturated dicarboxylic acid (oxalic acid, malonic acid, succinic acid, glutaric acid, adipic acid, pimelic acid, suberic acid, azelaic acid, sebacic acid, etc.); aliphatic oxydicarboxylic acid (d-tartaric acid etc.); amino acid (glutamic acid, aspartic acid, etc.); aliphatic unsaturated dicarboxylic acid (maleic acid, fumaric acid, itaconic acid, etc.); aromatic dicarboxylic acid (phthalic acid, isophthalic acid, terephthalic acid, etc.); tricarboxylic acid (trimellitic acid, citric acid, etc.); tetracarboxylic acid (pyromellitic acid, butanetetracarboxylic acid, cyclopentanetetracarboxylic acid, ethylenediaminetetraacetic acid, etc.); pentacarboxylic acid (diethylenetriaminepentaacetic acid, etc.); and the like.

Among them, preferable is polycarboxylic acid from the viewpoint of difficulty of denaturation of a protein and the like, further preferable is 2- to 8-valent polyvalent carboxylic acid, particularly preferable is tricarboxylic acid and tetracarboxylic acid, most preferable is tetracarboxylic acid.

The following is the pKa of main monovalent carboxylic acids.

Formic acid (3.7), acetic acid (4.8), propionic acid (4.9), butyric acid (4.8), isobutyric acid (4.9), valeric acid (4.8), caproic acid (4.9), enanthic acid (4.9), glycolic acid (3.8), lactic acid (3.9), gluconic acid (2.2), glycine (2.4), alanine (2.3), leucine (2.3)

The following is the pKa (pKa1) of main polyvalent carboxylic acids.

Oxalic acid (1.3), malonic acid (2.9), succinic acid (4.2), glutaric acid (4.3), adipic acid (4.4), azelaic acid (4.6), d-tartaric acid (3.0), maleic acid (1.9), fumaric acid (3.0), phthalic acid (2.9), isiophthalic acid (3.7), terephthalic acid (3.5), trimellitic acid (2.5), citric acid (3.2), pyromellitic acid (1.9), cyclopentanetetracarboxylic acid (2.9), ethylenediaminetetraacetic acid (2.0), glutamic acid (2.3), aspartic acid (2.0)

The following is the pKa (pKa1) of acids other than a carboxylic acid.

Phosphoric acid (2.2), pyrophosphoric acid (1.7), tripolyphosphoric acid (1.1), methylphosphoric acid (1.5), ethylphosphoric acid (1.6), boric acid (9.2), ascorbic acid (4.2)

Examples of the cationic part include the following quaternary ammonium cation (q1) and amine salt-type cation (q2).

From the viewpoint of bacteriolytic power, preferable is quaternary ammonium cation (q1).

Examples of the quaternary ammonium cation (q1) include a compound represented by the general formula (1):

(Chemical formula)

wherein, $R^1$, $R^2$, $R^3$ and $R^4$ are a linear or branched hydrocarbon group having 1 to 22 carbon atoms, at least one of $R^1$ to $R^4$ is a hydrocarbon group having 6 or more carbon atoms, and $R^1$ to $R^4$ may be the same or different from each other.

Examples of the hydrocarbon group represented by $R^1$ to $R^4$ in the quaternary ammonium cation (q1) include an aliphatic hydrocarbon group and an aromatic hydrocarbon group.

Examples of the aliphatic hydrocarbon group include a linear or branched alkyl group (methyl group, ethyl group, propyl group, n-butyl group, pentyl group, n-hexyl group, heptyl group, n-octyl group, nonyl group, decyl group, undecyl group, dodecyl group, i-, sec- and t-butyl group, 2-methylbutyl group, 2,2-dimethylpropyl group, 3-methylbutyl group, 2-ethylhexyl group, etc.) and an alkenyl group (vinyl group, allyl group, methallyl group, etc.).

Examples of the aromatic hydrocarbon group include a phenyl group, an arylalkyl group (benzyl group, phenylethyl group, phenylpropyl group, phenylbutyl group, etc.) and an alkylaryl group (methylphenyl group, ethylphenyl group, octylphenyl group, nonylphenyl group, decylphenyl group, dodecylphenyl group, etc.).

Examples of a preferable combination of a hydrocarbon group of $R^1$ to $R^4$ include the following (q11) to (q14).

(q11) Combination in which only one is an aliphatic hydrocarbon group having 6 to 22 carbon atoms, and other are an alkyl group having 1 to 4 carbon atoms;

Dodecyltrimethylammonium, tetradecyltrimethylammonium, hexadecyltrimethylammonium, octadecyltrimethylammonium, docecyldimethylethylammonium, tetradecyldimethylethylammonium, hexadecyldimethylethylammonium, octadecyldimethylethylammonium, dodecylmethyldiethylammonium, tetradecylmethyldiethylammonium, hexadecylmethyldiethylammonium, octadecylmethyldiethylammonium and the like.

(q12) Combination in which only two are an aliphatic hydrocarbon group having 6 to 22 carbon atoms, and other are an alkyl group having 1 to 4 carbon atoms;

Octyldecyldimethylammonium, dioctyldimethylammonium, didecyldimethylammonium, decyldodecyldimethylammonium, didodecyldimethylammonium, octyldecylmethylethylammonium, dioctylmethylethylammonium, didecylmethylethylammonium, didodecylmethylethylammonium, didecylmethylpropylammonium, didodecylethylpropylammonium, distearyldimethylammonium and the like.

(q13) Combination in which only one is an aromatic hydrocarbon group having 6 to 22 carbon atoms, and other are an alkyl group having 1 to 4 carbon atoms;

Benzyltrimethylammonium, benzyltriethylammonium, benzyltripropylammonium, benzylethyldimethylammonium and the like.

(q14) Combination in which only one is an aliphatic hydrocarbon group having 6 to 22 carbon atoms, only one is an aromatic hydrocarbon group having 6 to 22 carbon atoms, and other are an alkyl group having 1 to 4 carbon atoms;

Decyldimethylbenzylammonium, dodecyldimethylbenzylammonium, tetradecyldimethylbenzylammonium, hexadecyldimethylbenzylammonium, palm oil alkyldimethylbenzylammonium and the like.

Among (q1), from the viewpoint of bacteriolytic power, preferable is (q12), further preferable is one in which two of $R^1$ to $R^4$ are an alkyl group having 8 to 14 carbon atoms.

On the other hand, examples of the amine salt-type cation (q2) include primary to tertiary amine salt-type cations.

Examples of a primary amine constituting the primary amine cation include monoalkyl or cycloalkylamine having 6 to 18 carbon atoms (e.g. monohexylamine, monocyclohexylamine, monooctylamine, monododecylamine and the like).

Examples of a secondary amine constituting the secondary amine cation include dialkylamine in which at least one alkyl group has 6 to 18 carbon atoms (e.g. hexylmethylamine, octylethylamine, methyldodecylamine and the like).

Examples of a tertiary amine constituting the tertiary amine cation include trialkylamine in which at least one alkyl group has ######## carbon atoms (e.g. dimethyldodecylamine etc.).

As a method for producing the cationic surfactant (A), the following three methods are considered, being not limiting.

(1) A method, in which an alkyl carbonate salt of a quaternary ammonium cation and an equivalent amount of carboxylic acid are added, stirred, and reacted at 60 to 100° C. for 3 to 20 hours to exchange a salt, followed by purification. Examples of the alkyl group of the alkyl carbonate salt include an alkyl group having 1 to 4 carbon atoms, for example, a methyl group, an ethyl group, a propyl group and a butyl group.

(2) A method, in which quaternary ammonium halide is salt-exchanged with a strong basic salt of carboxylic acid, followed by purification. Examples of the strong basic salt of carboxylic acid include an alkali metal salt (sodium salt, potassium salt, etc.), an ammonium salt and an amine salt of carboxylic acid and the like.

(3) A method, in which quaternary ammonium hydroxide salt-exchanged with a strong basic salt of carboxylic acid, followed by purification. Examples of the strong basic salt of carboxylic acid include an alkali metal salt (sodium salt, potassium salt, etc.), an ammonium salt and an amine salt of carboxylic acid and the like.

As the bacteriolytic agent, upon use, the cationic surfactant (A) which is an essential component may be used as it is, or if necessary, is diluted with water, and can be used as a bacteriolytic agent aqueous diluted solution of a solution in water or a suspension in water.

The concentration of components other than water in the bacteriolytic agent aqueous diluted solution is appropriately selected depending on a bacterial cell which is a subject, a kind of a useful substance, and a kind of an extraction method, and is 0.01 to 99.9%, and preferably 0.1 to 50%.

The bacteriolytic agent, upon use, may contain, in addition to the cationic surfactant (A) as an essential component, a part or all of an organic solvent (B), other surfactant (C), and a solubility stabilizing agent (D), in advance in such a range that the effect of the present invention is not inhibited, or these may be used by appropriately incorporating them separately upon use.

In order to enhance solubility of the cationic surfactant (A) in water, if necessary, an organic solvent (B) may be added.

Examples of the organic solvent (B) include aliphatic alcohol-based solvents (methanol, ethanol, etc.), ketone-based solvents (acetone, methyl ethyl ketone, etc.), and carboxylic acid ester-based solvents (ethyl acetate, propyl acetate, methyl formate, etc.).

The proportion of the organic solvent (B) to be used is preferably not more than 10% by weight, further preferably not more than 5% (hereinafter, unless otherwise indicated, % indicates % by weight), and particularly preferably not more than 3% based on a weight of the bacteriolytic agent.

In the bacteriolytic agent, in order to further enhance bacteriolytic property, in addition to the cationic surfactant (A) as an essential component, other surfactant (C) having the synergistic effect can be appropriately added.

Examples of other surfactant (C) which is used for this purpose include one or more kinds selected from the following nonionic surfactant (C1), cationic surfactant (C2) other than (A), anionic surfactant (C3) and amphoteric surfactant (C4).

Nonionic Surfactant (C1)

(C11) Higher Alcohol Alkylene Oxide (Hereinafter, Abbreviated AO) Adduct:

Examples include an adduct (including block adduct and/or random adduct; the same hereinafter) of 1 to 20 mol of ethylene oxide (hereinafter, abbreviated as EO) and/or 1 to 20 mol of propylene oxide (hereinafter, abbreviated as PO) of a higher alcohol having 8 to 24 carbon atoms (decyl alcohol, dodecyl alcohol, palm oil alkyl alcohol, octadecyl alcohol and oleyl alcohol, etc.) (e.g. decyl alcohol EO (8 mol)/PO (7 mol) block adduct).

(C12) AO Adduct of Alkyl Phenol Having an Alkyl Group Having 6 to 24 Carbon Atoms:

Examples include an octyl or nonyl phenol EO (1 to 20 mol) and/or PO (1 to 20 mol) adduct (e.g. TRITON (registered trademark) X-100 and TRITON (registered trademark) X-114, etc.)

(C13) Polypropylene Glycol EO Adduct and Polyethylene Glycol PO Adduct:

Examples include a Pluronic-type surfactant and the like.

(C14) Fatty Acid AO Adduct:

Examples include an EO (1 to 20 mol) and/or PO (1 to 20 mol) adduct of a fatty acid having 8 to 24 carbon atoms (decanoic acid, lauric acid, myristic acid, palmitic acid, stearic acid, oleic acid and palm oil fatty acid, etc.).

(C15) Polyhydric Alcohol-Type Nonionic Surfactant:

Examples include an EO and/or PO adduct of 2- to 8-hydric polyhydric alcohol having 3 to 36 carbon atoms (glycerin, trimethylolpropane, pentaerythritol, sorbit and sorbitan, etc.); a fatty acid ester of the polyhydric alcohol and an EO adduct thereof (e.g. TWEEN (registered trademark) 20 and TWEEN (registered trademark) 80, etc.); alkyl glucoside (e.g. N-octyl-β-D-maltoside, n-dodecanoylsucrose, N-octyl-β-D-gulcopyranoside, etc.); as well as a fatty acid ester of sugar, a fatty acid alkanolamide and an AO adduct thereof (polyoxyethylene fatty acid alkanolamide, etc.). Examples of the fatty acid include the aforementioned ones.

Examples of the cationic surfactant (C2) other than (A) include cationic surfactants having one or more kinds of counterions selected from a halogen anion, a hydroxy anion, an alkyl sulfate anion and a superstrong acid anion as a counterion.

Examples of the halogen anion include a fluoride ion, a chloride ion, a bromide ion, an iodide ion and the like, examples of the alkyl sulfate anion include a methyl sulfate ion, an ethyl sulfate ion and the like, and examples of the superstrong acid anion include a tetrafluoroborate ion, a trifluoromethanesulfonate ion and the like.

Examples of the cation part constituting (C2) include the same cation part as that listed in (A).

Specific examples of (C2) include benzalkonium chloride, cetyltrimethylammonium bromide, and the like.

Examples of the anionic surfactant (C3) include an ether carboxylic acid or a salt thereof, an sulfate ester or an ether sulfate ester and a salt thereof, a sulfonate salt, a sulfosuccinate salt, a phosphate ester or an ether phosphate ester and a salt thereof, a fatty acid salt, an acylated amino acid salt, as well as naturally occurring carboxylic acid and a salt thereof (e.g. chenodeoxycholic acid, cholic acid, deoxycholic acid and the like), which each have a hydrocarbon group having 8 to 24 carbon atoms.

Examples of the amphoteric surfactant (C4) include a betaine-type amphoteric surfactant and an amino acid-type amphoteric surfactant.

Specifically, examples include amidosulfobetaine, cholamidopropyldimethylammonio propanesulfonic acid (CHAPS), cholamidoprpyldimethylammonio 2-hydroxypropane sulfonic acid (CHAPSO), carboxybetaine, lauroylsarcosine and methylbetaine.

Among other surfactants (C), a surfactant which is preferable in that bacteriolytic property is improved by using it in combination of the cationic surfactant (A) as an essential component is the nonionic surfactant (C1). A polyhydric alcohol-type nonionic surfactant (C15) is further preferable, a polyhydric alcohol fatty acid ester and an EO adduct thereof are particularly preferable, and TWEEN20, TWEEN (registered trademark) 80 are most preferable.

The proportion of other surfactant (C) to be used is preferably not more than 60%, further preferably not more than 40%, and particularly preferably not more than 20% from the viewpoint of difficulty of denaturation of a protein.

In addition, the content of (C) based on the content of (A) is preferably not more than 60%, and further preferably not more than 40% from the viewpoint of difficulty of denaturation of a protein.

From the viewpoint of difficulty of denaturation of a protein, the content of (C1) to (C4) based on a weight of (A) is as follows.

The content of (C1) is preferably not more than 50%, and further preferably not more than 30%, the content of (C2) is preferably not more than 20%, and further preferably not more than 10%, the content of (C3) is preferably not more than 20%, and further preferably not more than 10%, and the content of (C4) is preferably not more than 20%, and further preferably not more than 10%.

Examples of a stabilizing agent (D) for stabilizing solubility of the cationic surfactant (A) as an essential component in water and a solution of an aqueous solution thereof include a chelating agent, an organic acid and a salt thereof, and a polyhydric alcohol.

Examples of the chelating agent include ethylenediaminetetraacetic acid and a salt thereof, polyphosphoric acid and a salt thereof, and metaphosphoric acid and a salt thereof.

Examples of the organic acid and the salt thereof include lactic acid and a salt thereof, hyaluronic acid and a salt thereof, and the like.

Examples of the polyhydric alcohol include glycerin, sorbitol, mannitol, maltitol, pentaerythritol, xyltol, polyethylene glycol, proplylene glycol, and the like.

Among them, from the viewpoint of improvement in solubility, a polyhydric alcohol is preferable, and glycerin is further preferable.

A weight ratio (A)/(B)/(C)/(D) of respective components in the bacteriolytic agent of the present invention is preferably 20 to 100/0 to 10/0 to 30/0 to 70, further preferably 30 to 100/0 to 5/0 to 25/0 to 60, and particularly preferably 40 to 100/0 to 30/0 to 20/0 to 50 from the viewpoint of difficulty of denaturation of a protein.

In addition, a bacteriolytic enzyme such as lysozyme and the like may be appropriately used in combination.

Other embodiment of the present invention is a process for producing a useful substance from a useful substance-producing bacterium using the bacteriolytic agent.

Since a useful substance obtained by the process of the present invention for producing the useful substance is obtained by the aforementioned bacteriolysis method, it has a higher purity than that of the conventional one and, since it is excellent in bacteriolytic power, a high yield can be obtained.

Examples of the process of the present invention for producing the useful substance include a production process by the following order step. (One example of the case where a useful substance is a recombinant protein).

(1) Step of Culturing Protein:

A protein producing body such as *Escherichia coli* and the like is made to culture a recombinant protein.

(2) Bacteriolysis Step:

By using a bacteriolytic agent, an inclusion body in the protein producing body is taken out.

(3) Unfolding Step:

To an inclusion body suspension (e.g. 10 mg protein/mL) are added not less than 0.5 mol/L of an unfolding agent and not more than 20 mmol/L of a reducing agent, and the mixture is slightly stirred, and allowed to stand at room temperature for a few hours.

(4) Refolding Step:

To the unfolded protein suspension is added a refolding agent so as to be a concentration of 0.2 to 6 mol/L, and the mixture is slightly stirred, and allowed to stand at room temperature over night. Alternatively, refolding is performed by considerably diluting with a refolding buffer.

(5) Separation and Taking Out Step

An objective normal protein is separated and taken out from the suspension by column chromatography and the like.

Examples of the protein producing body in the step of culturing a protein of (1) include the following bacterium cells.

Examples of the bacterium cell include Streptococci, Staphylococci, *Escherichia, Streptomyces* and *Bacillus* cells, fungal cells: e.g. yeast cells and *Aspergillus* cells, insect cells: e.g. DrosophilaS2, SpodopteraSf9 cells, animal cells: e.g. CHO, COS, Hela, C127, 3T3, BHK, 293 and Bows melanoma cells as well as plant cells.

Examples of *Escherichia* include *E. coli* K12DH1 [see Proc. Natl. Acad. Sci. U.S.A. vol. 60, pp. 160 (1968)], JM103 [see Nucleic Acids Research vol. 9, pp. 309 (1981)], JA221 [see Journal of Molecular Biology vol. 120, pp. 517 (1978)], HB101 [see Journal of Molecular Biology vol. 41, pp. 459 (1969)], C600 [see Genetics vol. 39, pp. 440 (1954)], MM294 [see Nature vol. 217, pp. 1110 (1968)] [the disclosure content disclosed in the above Reference Publications is hereby incorporated].

Examples of *Bacillus* include *Bacillus subtilis* MI114 [see Gene, vol. 24, pp. 255 (1983)], 207-21 [see Journal of Biochemistry vol. 95, pp. 87 (1984)] [the disclosure content disclosed in the above Reference Publications is incorporated by reference].

Examples of a process for producing a recombinant protein include the following methods:

(i) A messenger RNA (mRNA) is separated from an objective protein-producing cell, from the mRNA, a single-stranded cDNA, and then, a double-stranded DNA is synthesized, and the complementary DNA is incorporated into a phage or a plasmid.

(ii) A host is transformed with the resulting recombinant phage or plasmid, and cultured, and then a phage or a plasmid containing an objective DNA is isolated by hybridization with a DNA probe encoding a part of an objective protein, or an immunoassay method using an antibody.

(iii) From the recombinant DNA, an objective cloned DNA is excised, the cloned DNA or a part thereof is ligated downstream of a promoter in an expression vector.

Thereafter, by a suitable method, a host is transformed with an expression vector, and is cultured. Culturing is performed usually at 15 to 43° C. for 3 to 24 hours and, if necessary, ventilation or stirring may be added.

In the bacteriolysis step of (2), for example, in the case of *Escherichia coli*, an inclusion body produced in a bacterium cell is taken out by dissolving a phospholipid layer of an outer membrane and/or a peptideglucan layer of an internal membrane, or destructing a part thereof, using the bacteriolytic agent of the present invention.

In the unfolding step of (3), examples of the unfolding agent used in the unfolding step of disintegrating a three-dimensional structure of a protein with the unfolding agent to perform unfolding after use of the bacteriolytic agent of the present invention include guanidine hydrochloride, urea, combination use of them and the like.

In addition, when a protein is a protein containing a S—S bond in a molecule, as a reducing agent, in addition to guanidine hydrochloride and/or urea, 2-mercaptoethanol, dithiothreitol, cystine, thiophenol or the like may be added.

In a method of refolding a protein in the refolding step of (4), refolding can be performed by any method of a dilution method, a dialysis method, a surfactant utilizing method, an artificial shaperon utilizing method and a method described in Japanese Patent Application No. 2005-235980. Particularly, the method described in Japanese Patent Application No. 2005-235980 is preferable from the viewpoint of productivity and general use.

Examples of a filler used in column chromatography in a step of separating and taking out a protein of (5) include silica, dextran, agarose, cellulose, acrylamide, vinyl polymer and the like, and as a commercially available product, there are Sephadex series, Sephacryl series, Sepharose series (all, Pharmacia), and Bio-Gel series (Bio-Rad), and they are available.

Examples of the useful substance in the process for producing the useful substance of the present invention include a protein (P1), an amino acid (P2), a nucleic acid (P3), an antibiotic (P4), an antibody (P5), sugars (P6) and vitamins (P7).

Examples of the protein (P1) include an enzyme (P1-1), a recombinant protein (P1-2), and a peptide (P1-3).

Examples of the enzyme (P1-1) include a hydrolase, an isomerase, an oxidoreductase, a transferase, a synthase, a lyase, and the like.

Examples of the hydrolase include protease, serine protease, amylase, lipase, cellulase, glucoamylase, and the like.

Examples of the isomerase include glucose isomerase.

Examples of the oxidoreductase include peroxidase, and the like.

Examples of the transferase include acyltransferase, sulfotransferase, and the like.

Examples of the synthase include fatty acid synthase, phosphoric acid synthase, citric acid synthase, and the like.

Examples of the lyase include pectin lyase, and the like.

Examples of the recombinant protein (P1-2) include a protein preparation, a vaccine, and the like.

Examples of the protein preparation include interferon α, interferon β, interleukins 1 to 12, growth hormone, erythropoietin, insulin, granular colony stimulating factor (G-CSF), tissue plasminogen activator (TPA), natriuretic peptide, blood configuration factor VIII, somamedin, glucagon, growth hormone releasing factor, serum albumin, calcitonin, and the like.

Examples of the vaccine include hepatitis A vaccine, hepatitis B vaccine, hepatitis C vaccine, and the like.

The peptide (P1-3) is not particularly limited in an amino acid composition, and examples include dipeptide, a tripeptide, and the like.

Examples of the amino acid (P2) include glutamic acid, tryptophan, alanine, dipeptide, and the like.

Examples of the nucleic acid (P3) include deoxyribonucleic acid (DNA), and ribonucleic acid (RNA).

Examples of the antibiotic (P4) include streptomycin, vancomycin, and the like.

Examples of the antibody (P5) include a monoclonal antibody and a polyclonal antibody.

Examples of the sugars (P6) include hyaluronic acid, albumin, ceramide, erythritol, trehalose, lipopolysaccharide, cyclodextrin, and the like.

Examples of vitamins (P7) include vitamins A and a derivative thereof as well as a salt thereof, vitamins B such as vitamin B6, vitamin B12 and the like, and a derivative thereof as well as a salt thereof, vitamins C and a derivative thereof as well as a salt thereof.

Among them, the bacteriolytic agent of the present invention is suitable in producing (P1) and (P2), particularly (P1).

Other embodiment of the present invention is a protein, an amino acid, a nucleic acid, an antibiotic, an antibody, sugars or vitamins obtained by the useful substance producing process, and examples include the aforementioned ones. Among them, preferable is (P1) and (P2), particularly (P1).

EXAMPLES

The present invention will be further described by the following Examples and Comparative Examples, but the present invention is not limited to them.

Example 1

Into a 50 ml-Erlenmeyer flask was placed 16.04 g of methyl carbonate salt of didecyldimethylammonium (0.04 equivalent in terms of a cationic group), and 2.46 g of cyclopentanetetracarboxylic acid (0.04 equivalent as a carboxyl group) was added a small amount at a time while being stirred. The mixture was continuously stirred for 8 hours while being warmed to 80° C. with a constant temperature bath equipped with a stirrer, carbon dioxide and methanol were released to the outside of a system, and 15.49 g (yield 99.9%) of a cyclopentane tetracarboxylic acid salt of didecyldimethylammonium was obtained. The pKa of cyclotentanetetracarboxylic acid is 2.9.

Further, 30 parts of glycerin, 2 parts of TWEEN 80 and 18 parts of water were added to 50 parts of the resulting cationic surfactant to make a bacteriolytic agent of the present invention.

Example 2

According to the same manner as that of Example 1 except that cyclopentanetetracarboxylic acid of Example 1 was changed to citric acid, a citric acid salt of didecyldimethylammonium was obtained, and glycerin, TWEEN 80 and water were similarly added to make a bacteriolytic agent of the present invention. The pKa of citric acid is 3.2.

Example 3

According to the same manner as that of Example 1 except that cyclopentanetetracarboxylic acid of Example 1 was changed to adipic acid, an adipate salt of didecyldimethylammonium was obtained, and glycerin, TWEEN 80 and water were similarly added to make a bacteriolytic agent of the present invention. The pKa of adipic acid is 4.4.

Example 4

According to the same manner as that of Example 1 except that cyclopentanetetracarboxylic acid of Example 1 was changed to acetic acid, an acetate salt of didecyldimethylammonium was obtained, and glycerin, TWEEN 80 and water were similarly added to make a bacteriolytic agent of the present invention. The pKa of acetic acid is 4.8.

Example 5

According to the same manner as that of Example 1 except that a methyl carbonate salt of didecyldimethylammonium of Example 1 was changed to a methyl carbonate salt of distearyldimethylammonium, a cyclopentanetetracarboxylic acid salt of distearyldimethylammonium was obtained, and glycerin, TWEEN 80 and water were similarly added to make a bacteriolytic agent of the present invention. The pKa of cyclopentanetetracarboxylic acid is 2.9.

<Assessment>

Using bacteriolytic agents made in Examples 1 to 5, bacteriolytic power, difficulty of denaturation of a protein and productivity of sugars were assessed.

On the other hand, using, as a comparative bacteriolytic agent (Comparative Examples 1 to 3), a solution of a lauryl amine EO (2 mol) adduct in xylene (xylene is 70%), a mixture of tetradecyl and pentadecyl alcohol (weight ratio 6/4) EO (2 mol) adduct, and didecyldimethylammonium chloride were assessed according to the same manners as those of Examples.

An assessment method is as follows.

<Bacteriolytic Power>

Into a 2 ml-screw tube were added 0.5 ml of a solution of an *Escherichia coli* (*E-coli*) cell and 50 µl of a bacteriolytic agent aqueous diluted solution which had been diluted so as to be a concentration of 50% as a surfactant with a micropipette, and the mixture was mixed well. The mixture was stored by allowing to stand at 20° C. for 3 days, which was used as a sample, and the number of bacterium cells was measured with a super deep profile measurement microscope (manufactured by KEYENCE CORPORATION, VK-8500). Bacteriolytic power was calculated by a following equation. Results are shown in Table 1.

As a blank, 50 µl of ion-exchanged water was used in place of a bacteriolytic agent aqueous diluted solution.

Bacteriolytic power (%)=[1−(the number of bacterial cells in sample after 3 days/the number of bacterial cells of blank)]×100

Determination Criteria:

| Bacteriolytic power $\geq$ 80% | 5 score |
|---|---|
| 60% $\leq$ Bacteriolytic power < 80% | 4 score |
| 40% $\leq$ Bacteriolytic power < 60% | 3 score |
| 20% $\leq$ Bacteriolytic power < 40% | 2 score |
| Bacteriolytic < 20% | 1 score |

<Denaturation Resistance: Difficulty of Denaturation of Protein>

The difficulty was assessed as a denaturation degree of a cellulase.

To a 2 ml-tube for centrifugation were added 0.6 ml of a 1% cetylmethylcellulose aqueous dispersion, 0.6 ml of a bacteriolytic agent aqueous diluted solution which had been diluted so as to be a concentration of 0.2% as a surfactant, and 10l of a 100 ppm aqueous solution of cellulase (manufactured by Nagase, cellulase HT), and the tube was swung to mix the materials. After allowing to stand at 37° C. for 5 minutes, the mixture was centrifuged (10,000 rpm×3 minutes) with a centrifuge (Microfuge. 11 manufactured by Beckmann), and the an upper layer was separated and recovered. Into a 20 ml-test tube were placed 0.25 ml of the upper layer, 0.25 ml of ion-exchanged water and 0.5 ml of a 5% phenol aqueous solution, followed by mixing.

Further, 2.5 ml of concentrated sulfuric acid was added, the tube was allowed to stand at room temperature for 10 minutes, mixed and allowed to stand at 20° C. for 20 minutes to obtain a sample solution. The absorbance of the sample solution at 490 nm (absorption of a product from degradation of cetylmethylcellulose with an enzyme) was measured with a ultraviolet visible spectrometer (UV-2550 manufactured by Shimadzu Corporation). As a blank, 0.6 ml of ion-exchanged water was used in place of a bacteriolytic water-diluted solution. When in a step of bacteriolysis step, cellulase (enzyme) is not denatured, activity is reserved, and cetylmethylcellulose is effectively degraded, absorbance is increased (becomes absorbance near that of the blank).

Difficulty of denaturation of a protein was calculated by the following equation, and assessed by the following determination criteria.

Results are shown in Table 1.

Difficulty of denaturation of protein (%)=(absorbance of sample solution/absorbance of blank)×100

Determination Criteria

Difficulty of denaturation of protein $\geq$ 90% - - - 5 score
70%$\leq$difficulty of denaturation of protein <90% - - - 4 score
50%$\leq$difficulty of denaturation of protein <70% - - - 3 score
30%$\leq$difficulty of denaturation of protein <50% - - - 2 score
Difficulty of denaturation of protein <30% - - - 1 score <Productivity of Sugars>

The productivity was assessed as productivity of hyaluronic acid.

One liter of a medium consisting of 5% glucose, 0.2% primary potassium phosphate, 1.0% polypeptone and 0.5% yeast extract was heat-sterilized, inoculated with *Streptococcus mutans*, and cultured at 37° C. for 2 days under stirring. Each bacteriolytic agent was added to a medium after culturing so as to be a final concentration of 0.4% by weight, the medium was stirred for 1 hour, and pieces of a bacterial cell were removed by centrifugation, the supernatant was ethanol-precipitated two times, and this precipitate was vacuum-dried at 40° C. to obtain purified hyaluronic acid.

Productivity of sugars was assessed from a yield (g/L) of hyaluronic acid using the following determination criteria. Results are shown in Table 1.

Determination Criteria

Yield of hyaluronic acid $\geq$ 5 (g/L) - - - 5 score
3 (g/L)$\leq$yield of hyaluronic acid $\geq$ 5 (g/L) - - - 3 score
Yield of hyaluronic acid <3 (g/L) - - - 1 score

TABLE 1

| | | Cationic surfactant (A) | Bacteriolytic power (score) | Denaturation resistance (score) | Productivity (score) |
|---|---|---|---|---|---|
| Example | 1 | Didecyldimetylammonium-cyclopentanetetracarboxylic acid salt | 5 | 5 | 5 |
| | 2 | Didecyldimethylammonium-citric acid salt | 5 | 5 | 5 |
| | 3 | Didecyldimethylammonium-adipic acid salt | 5 | 4 | 5 |
| | 4 | Didecyldimethylammonium-acetic acid salt | 5 | 4 | 5 |
| | 5 | Distearyldimethylammonium-cyclopentanetetracarboxylic acid salt | 4 | 5 | 5 |
| Comparative Example | 1 | Laurylamine EO (2 mol) adduct solution in xylene | 2 | 2 | 1 |
| | 2 | Tetradecyl-pentadecyl alcohol mixture EO (2 mol) adduct | 1 | 2 | 1 |
| | 3 | Didecyldimethylammonium chloride | 4 | 3 | 3 |

INDUSTRIAL APPLICABILITY

The bacteriolytic agent of the present invention can be used in a step of extracting a useful substance such as a protein and the like from a producing bacterium. Examples of the useful substance include a protein, an amino acid, a nucleic acid, an antibiotic, sugars or vitamins. Alternatively, the bacteriolytic agent of the present invention can be utilized as a vector for introducing a gene into a cell and, further, can be also utilized as a cell destructing agent in combination use of the bacteriolytic agent of the present invention and an enzyme and the like.

The invention claimed is:

1. A bacteriolytic agent comprising a cationic surfactant, wherein the cationic surfactant is at least one selected from the group consisting of didecyldimethylammonium-cyclopentanetetracarboxylic acid salt, and distearyldimethylammonium-cyclopentanetetracarboxylic acid salt.

2. The bacteriolytic agent according to claim 1, further comprising:
   other surfactant than the cationic surfactant; and
   water.

* * * * *